(12) United States Patent
Tyagi et al.

(10) Patent No.: US 7,511,135 B2
(45) Date of Patent: Mar. 31, 2009

(54) METHOD FOR MANUFACTURE OF CEFTIOFUR

(75) Inventors: Om Dutt Tyagi, Maharashtra (IN); Santosh Kumar Richhariya, Maharashtra (IN); Rajesh Kumar Ramchandra Pawar, Maharashtra (IN); Yuvaraj Atmaram Chavan, Maharashtra (IN)

(73) Assignee: Lupin Limited, Maharashtra (IN)

( * ) Notice: Subject to any disclaimer, the term of this patent is extended or adjusted under 35 U.S.C. 154(b) by 480 days.

(21) Appl. No.: 10/532,194

(22) PCT Filed: Oct. 27, 2003

(86) PCT No.: PCT/IN03/00345

§ 371 (c)(1),
(2), (4) Date: Sep. 13, 2005

(87) PCT Pub. No.: WO2004/039811

PCT Pub. Date: May 13, 2004

(65) Prior Publication Data

US 2006/0149054 A1     Jul. 6, 2006

(30) Foreign Application Priority Data

Oct. 29, 2002   (IN)   ................. 937/MUM/2002

(51) Int. Cl.
C07D 501/36   (2006.01)
(52) U.S. Cl. .................................... 540/227
(58) Field of Classification Search .......... None
See application file for complete search history.

(56) References Cited

U.S. PATENT DOCUMENTS

| 4,937,330 A | 6/1990 | Sacks et al. |
| 6,388,070 B1 | 5/2002 | Deshpande et al. |

OTHER PUBLICATIONS

Abstract for Zhongguo Yiyao Gongye Zazhi (2001), 32(6), 241-242.

*Primary Examiner*—Mark L Berch
(74) *Attorney, Agent, or Firm*—Ladas and Parry LLP

(57) ABSTRACT

A process for preparation of ceftiofur of formula (I)

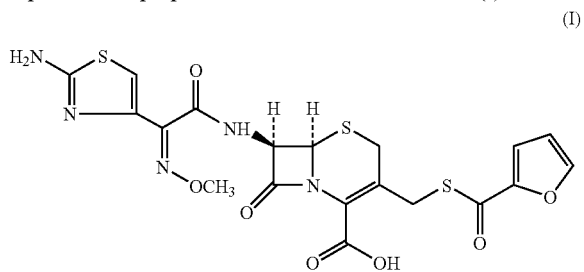

having purity greater than 97% is disclosed. The process comprises reacting [2-(2-aminothiazol-4-yl)]-2-syn-methoxyimino acetic acid-2-benzothiazolyl thioester of formula (II),

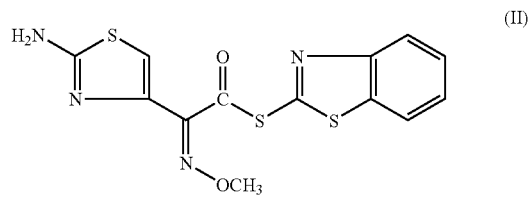

with 7-amino-3-(2-furanylcarbonylthiomethyl)-3-cephem-4-carboxylic acid of formula (III)

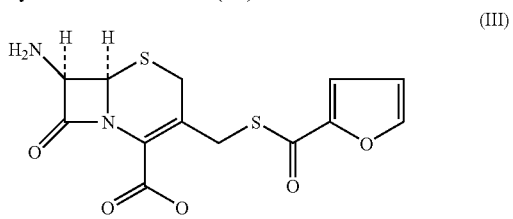

in the presence of a mixture of an water-immiscible inert organic solvent and water and in the presence of a organic base and isolating ceftiofur of formula (I) substantially free of impurities by,
 a) adding water to the reaction mixture and selectively partitioning the impurities in the organic phase and ceftiofur (I) in the form of a salt with the base in the aqueous phase,
 b) acidifying the aqueous phase containing ceftiofur (I) in the form of a salt with the base in the presence of a mixture containing a water-miscible and a water-immiscible organic solvent and in the presence of a saturated aqueous solution of an alkali or alkaline earth containing salt, to partition ceftiofur (I) in the organic phase, and
 c) isolating ceftiofur (I) of high purity and substantially free of impurities by evaporation of the organic solvent or precipitation by addition of a anti-solvent.

19 Claims, No Drawings

METHOD FOR MANUFACTURE OF CEFTIOFUR

FIELD OF THE INVENTION

The present invention relates to an improved method for manufacture of Ceftiofur in high purity. In particular, the present invention relates to an improved method for manufacture of Ceftiofur substantially free from impurities.

BACKGROUND OF THE INVENTION

Ceftiofur is a broad-spectrum third generation antibiotic, which is primarily used for veterinary use. It is known chemically as (6R, 7R)-7-[[(2Z)-(2-amino-4-thiazolyl) (methoxyimino)acetyl]amino]-3-[[(2-furanylcarbonyl)thio]methyl]-8-oxo-5-thia-1-azabicyclo[4.2.0]oct-2-ene-2-carboxylic acid and is represented by the formula (I).

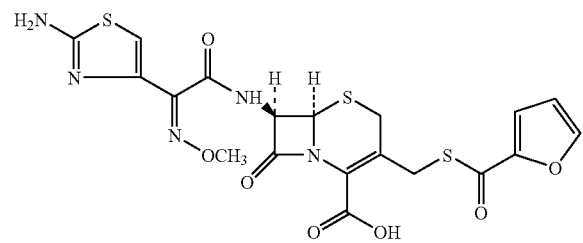

Ceftiofur is commercially sold as the sodium salt and is marketed under the brand names Naxcel® and Excenel® for parenteral administration, in bovine animals.

Ceftiofur has been synthesized by any of the following three methods, viz,

I. Ceftiofur and its salts thereof, especially the sodium salt is described in U.S. Pat. No. 4,464,367 (Labeeuw et. al). The patent describes two methods for preparation of Ceftiofur (I) comprising, i) amidification at the 7-position of 7-amino-3-thiomethyl furoyl-3-cephem-4-carboxylic acid with a suitably activated [(2Z)-(2-tritylamino-4-thiazolyl) methoxyimino] acetic acid derivative such as mixed anhydride or an activated ester to give ceftiofur (I) after necessary deprotection.

ii) functionalisation at the 3-position of a 7-[2-(2-aminothiazol-4-yl)-2-syn-methoxyimino] acetamido cephalosporanic acid i.e. cefotaxime acid, with thiofuroic acid to give Ceftiofur (I).

U.S. Pat. No. 4,464,367 contains enabling disclosure for preparation of ceftiofur as per method (I) comprising reaction of 7-amino-3-thiomethyl furoyl-3-cephem-4-carboxylic acid with the syn isomer of (2-tritylaminothiazol-4-yl)-2-methoxyimino acetic acid activated with 1-hydroxy benzotriazole, followed by removal of the trityl protecting group to give ceftiofur (I).

However, for method (II), apart from the reaction sequence given in column 3, lines 25-35 depicting conversion of cefotaxime to ceftiofur (I), there is no enabling disclosure whatsoever about how the conversion could be carried out.

The two methods for preparation of ceftiofur of formula (I) are summarized in scheme (I).

Scheme I: Method for preparation of ceftiofur (I) as disclosed in U.S. Pat. No. 4,464,367

Method-I:

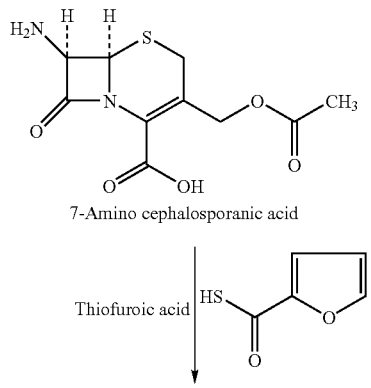

7-Amino cephalosporanic acid

Thiofuroic acid

Method-II:

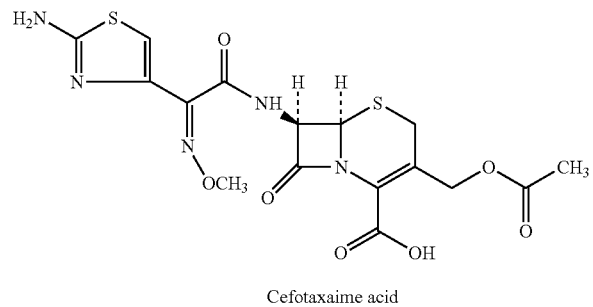

Cefotaxaime acid

-continued

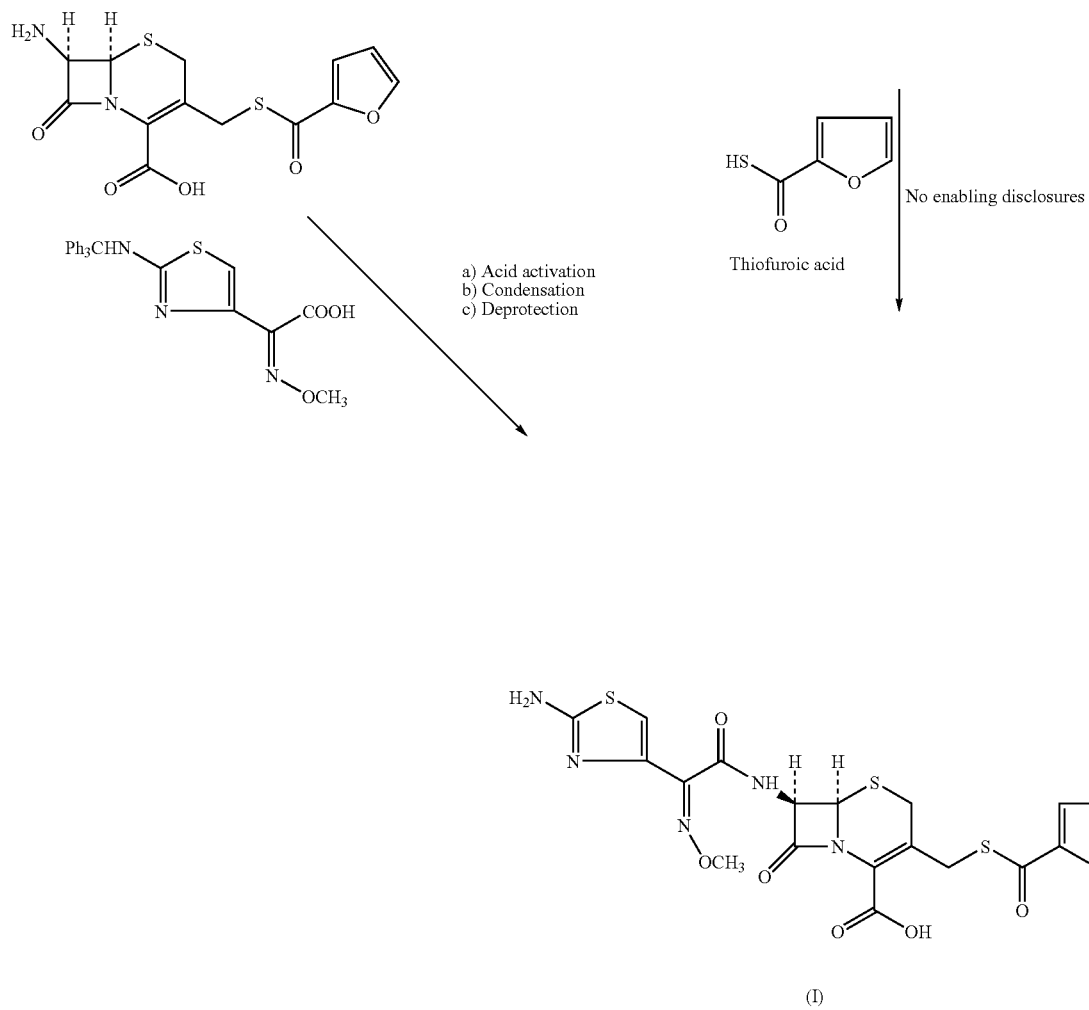

Further, synthesis of ceftiofur as per method-I involves additional steps of protection of the amino group of [2-(2-aminothiazol-4-yl)]-2-syn methoxyimino acetic acid with trityl chloride followed by deprotection in presence of formic acid to give ceftiofur of formula (I). The amidification method utilises toxic, expensive dicyclohexyl carbodiimide for preparing the activated ester of [2-(2-aminothiazol-4-yl)]-2-syn methoxyimino acetic acid with 1-hydroxy benzotriazole, resulting in the formation of dicyclohexyl urea, which is difficult to remove.

II. Although, the claims of U.S. Pat. No. 6,458,949 B1 (Handa, et al) appear to be obvious, over prior art described in EP Patent No. 0,302,94, U.S. Pat. Nos. 5,109,135, and 5,109,131 the said patent however discloses another method for the preparation of Ceftiofur (I), which is summarized in scheme-II.

The method comprises, reaction of 4-halo-3-oxo-2-methoxyimino butyric acid, activated as the acid halide, with sylated 7-amino-3-thiomethyl furoyl-3-cephem-4-carboxylic acid to give the corresponding 7-carboxamido derivative which on subsequent treatment with thiourea gives ceftiofur of formula (I). Herein, the thiazole ring is formed after the amidification step with thiourea.

Scheme-II: Method for preparation (I) as disclosed in U.S. Pat. No. 6,458,949 B1

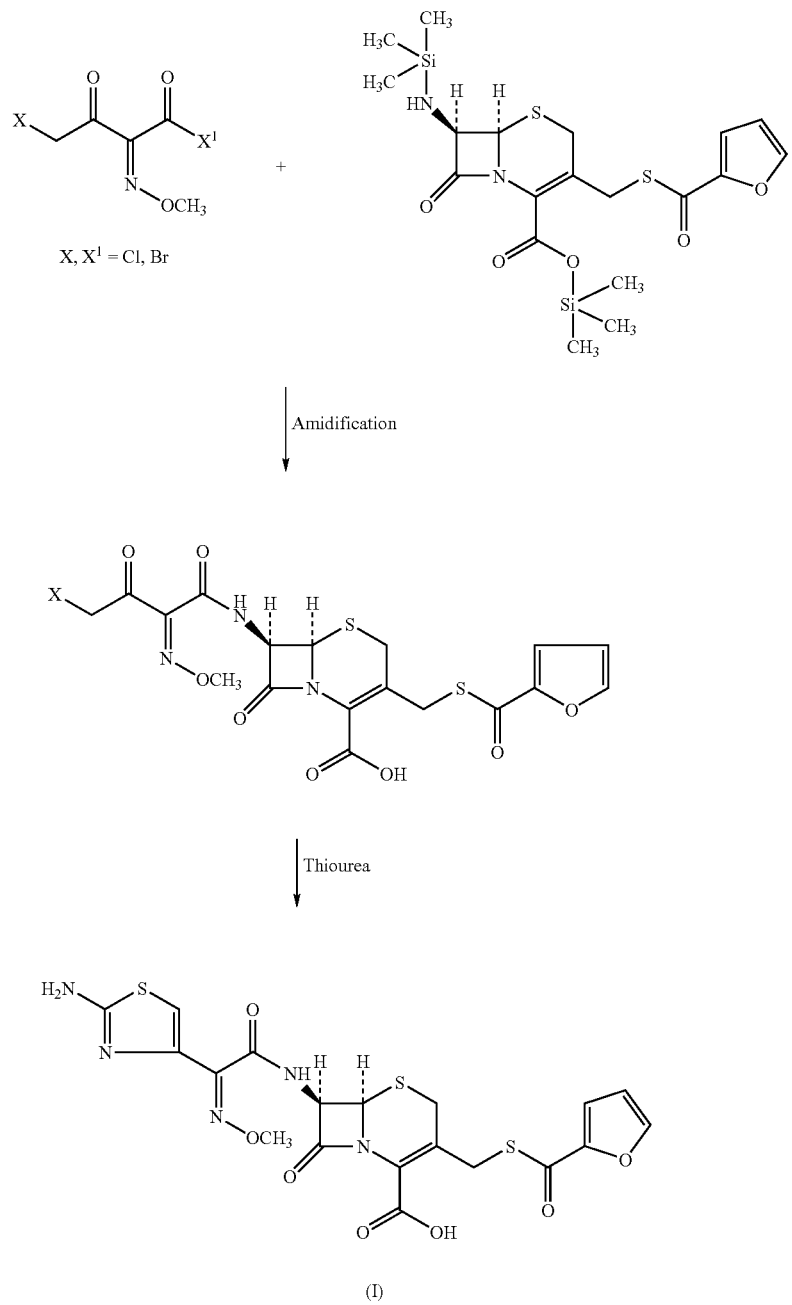

(I)

The method described in U.S. Pat. No. 6,458,949 B1 is complicated and tedious, as it involves initial preparation of 4-halo-3-oxo-2-methoxyimino butyric acid requiring four steps followed by subsequent amidification reaction with 7-amino-3-thiofuroylmethyl-3-cephalosporanic acid and cyclisation with thiourea. The overall yield of (I) is therefore low, rendering the method commercially not very attractive.

III. U.S. Pat. No. 6,388,070 (Deshpande, et. al) teaches a method for synthesis of ceftiofur (I), and other cephalosporin compounds like ceftriaxone and ceftazidime, cefixime, cefpodoxime acid, cefetamet and cefotaxime acid.

Herein, [2-(2-aminothiazol-4-yl)]-2-syn methoxyimino acetic-acid is activated as the thioester by reaction with 2-mercapto-5-phenyl-1,3,4-oxadiazole in the presence of bis-(2-oxo-oxazidinyl)phosphinic chloride. The thioester on reaction with silylated 7-amino-3-substituted-3-cephem compounds in the presence of a base at low temperatures gives the corresponding 7-acylamido-3-substituted-3-cephem cephalosporin, depicted in scheme-III, herein below:

Various reactive derivatives of [2-(2-aminothiazol-4-yl)]-2-oxyimino acetic acid compounds have been utilized for synthesis of several 3-substituted cephalosporin antibiotics

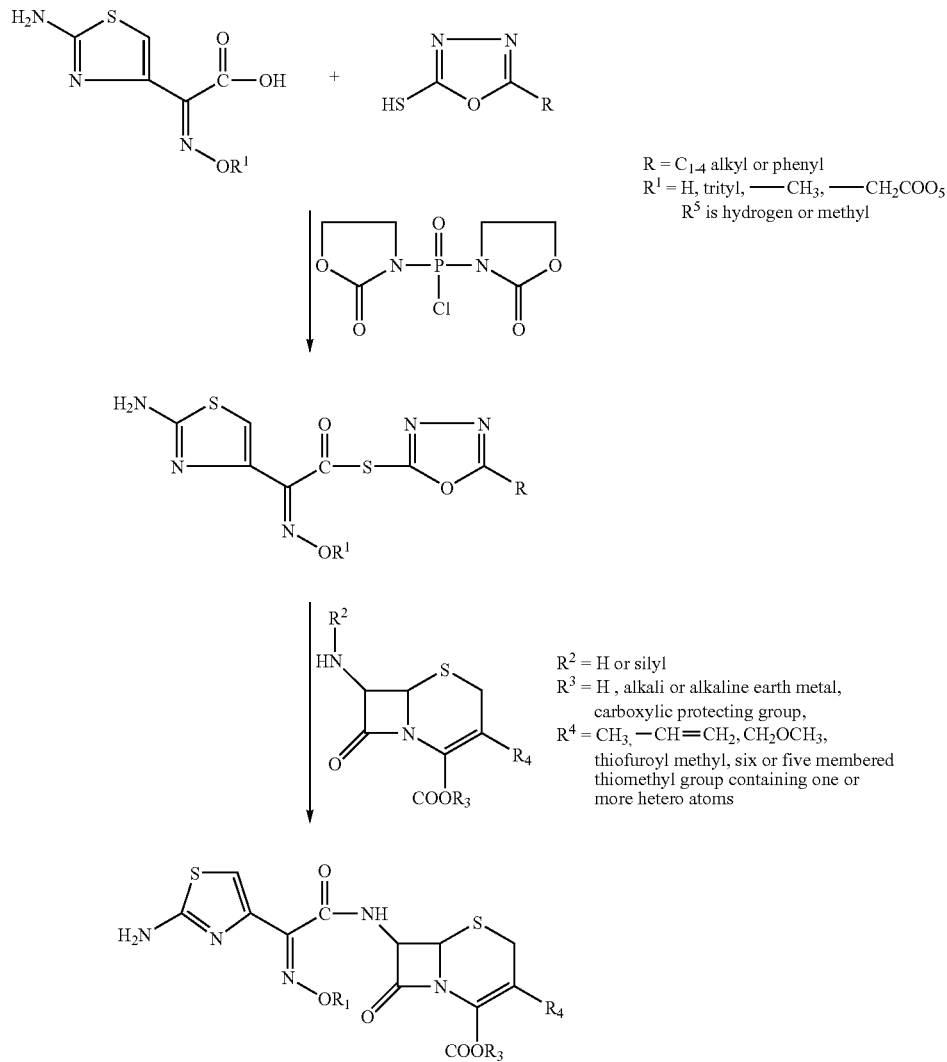

The activation of [2-(2-aminothiazol-4-yl)]-2-syn methoxyimino acetic acid with 2-mercapto-5-phenyl-1,3,4-oxadiazole is quite slow and it requires a time upto 34 hours. Moreover, the method utilizes a reagent like bis-(2-oxo-oxazidinyl)phosphinic chloride which is expensive.

Apart from the above methods, which utilize activation of the carboxylic acid moiety of either the [2-(2-aminothiazol-4-yl)]-2-syn methoxyimino acetic acid or 4-halo-3-oxo-2-methoxyimino butyric acid through the formation of a mixed anhydride or activated ester with 1-hydroxy benzotriazole or 2-mercapto-5-phenyl-1,3,4-oxadiazole or an acid chloride, there are no reports of synthesis of ceftiofur (I) by other methods, specially through utilization of other reactive derivatives of the said carboxylic compounds.

carrying a [2-(2-aminothiazol-4-yl)]-2-oxyimino acetamido addendum in the 7-position. These include, to a name a few a) an acyloxypliosphonium halide derivative as disclosed in U.S. Pat. No. 5,317,099 (Lee et. al) for synthesis of cefotaxime and ceftriaxone;

b) an acetyl sulfite dialkyl formiminium halide hydrohalide derivative as disclosed in U.S. Pat. No. 5,037,988 (Meseguer et. al) for synthesis of cefotaxime, ceftriaxone, cefmenoxime, ceftizoxime, and ceftazidime;

c) a dialkyl chloro thiophosphate ester as disclosed in U.S. Pat. No. 5,567,813 (Sung et. al) for synthesis of cefotaxime, ceftriaxone, cefemenoxime, ceftizoxime, cefpirome sulfate and cefepime;

d) a dimethyl forminium chloride chlorosulphate derivative as disclosed in U.S. Pat. No. 5,739,346 (Datta et. al) for synthesis of cefotaxime, ceftriaxone, ceftazidime, cefazolin etc.

A reactive derivative of [(2)-(2-aminothiazol-4-yl)]-2-syn-oxyimino acetic acid compounds widely utilized in cephalosporin chemistry for effecting amidification at 7-position is the 2-benzothiazolyl thioester, first disclosed in U.S. Pat. No. 4,767,852 (Ascher et. al), the chemistry of which is shown hereinbelow.

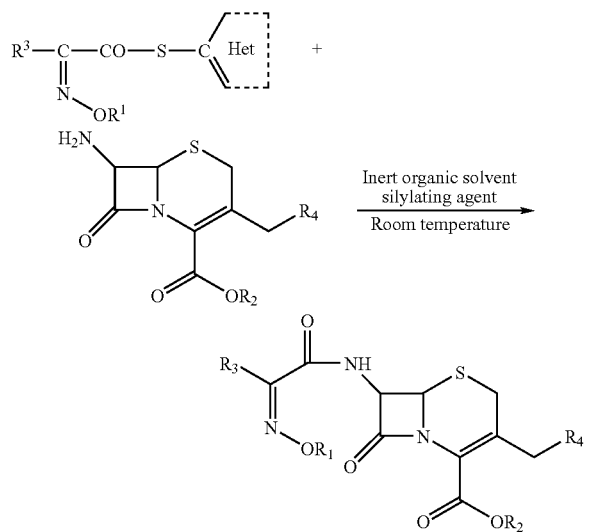

wherein the groups $R^1$ to $R^3$ are as defined therein and the group $R^4$ is an acetoxy, carbamoyloxy, or is a group of formula S—Y, wherein Y is a heterocyclic ring.

The cephalosporin compounds that fall under the definition of the group $R^4$ of this patent include the commercially and therapeutically valuable cephalosporin antibiotics like cefotaxime, ceftriaxone and cefuzonam.

The group $R^4$ of U.S. Pat. No. 4,767,852 does not encompass ceftiofur as it covers only those 3-thiomethyl compounds in which the sulphur atom is directly attached to a heterocyclic ring, and not those compounds in which a carbonyl group is interposed between S and Y, where Y is a heterocyclic ring Ceftiofur (I) has a carbonyl group interposed between S and Y i.e. between the 3-thiomethyl group and the furan ring.

The method disclosed in U.S. Pat. No. 4,767,852, as is evident from description given in the examples of the said patent, essentially consists reaction of a protected 7-amino-3-substituted cephalosporanic acid derivative, in particular a (N,O)-bis silylated 7-amino-3-substituted cephalosporanic acid derivative with the [2-(2-aminothiazol-4-yl)]-2-syn-oxyimino acetic acid-2-benzothiazolyl thioester in an inert organic solvent at ambient temperature for a time ranging between 0.5 to 48.0 hours to give the object [2-(2-aminothiazol-4-yl)]-2-syn-oxyimino acetamido-3-substituted-3-cephem-4-carboxylic acid compounds such as cefotaxime, ceftriaxone and cefuzonam, which it should be noted carries "a residue of a nucleophile at the 3α-position".

From the abovementioned methods it is apparent that the preparation of the [2-(2-aminothiazol-4-yl)]-2-oxyimino acetamido-3-substituted-3-cephem4-carboxylic acid compounds is effected essentially in an inert organic solvent, thereby implying a reaction medium free of water and through utilization of a protected 7-amino-3-substituted cephalosporanic acid derivative as the starting material.

In addition, the [2-(2-aminothiazol-4-yl)]-2-oxyimino acetic acid-2-benzothiazolyl thioester has also been utilized for synthesis of other [2-(2-aminothiazol-4-yl)]-2-oxyimino acetamido-3-substituted-3-cephem-4-carboxylic acid compounds such as cefixime as disclosed in U.S. Pat. No. 6,313,289. Here again, the method comprises reacting a protected 7-amino-3-substituted cephalosporanic acid derivative, particularly a protected 7-amino-3-vinyl-3-cephem-4-carboxylic acid, wherein the amino group and the carboxylic group are protected as trialkylsilyl group with a [2-(2-aminothiazol-4-yl)]-2-methoxyimino acetic acid-2-benzothiazolyl thioester in the form of a aqueous solution of a crystalline solvate with dimethyl acetamide and an inert organic solvent medium at room temperature in the presence of a base to give cefixime after removal of the said protective groups.

Cefixime is isolated as the salt of an organic base or as an acid addition salt with sulphuric acid.

In their attempt to extend the method described in U.S. Pat. Nos. 4,767,852 and 6,313,289, for synthesis of ceftiofur the present inventors found to their surprise that when (N,O)-bis silyl-7-amino-3-thiofuroylmethyl-3-cephalosporanic acid of formula ($III^1$),

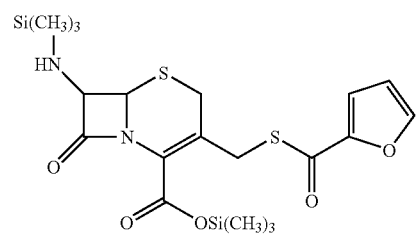

is reacted with [2-(2-aminothiazol-4-yl)]-2-methoxyimino acetic acid-2-benzothiazolyl thioester (MAEM) of formula (II),

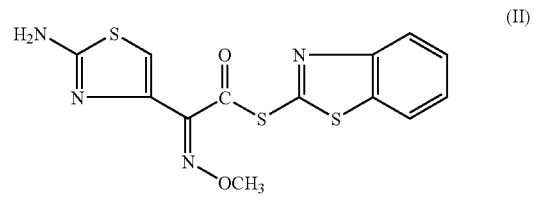

in an inert organic solvent (dichloromethane) in the presence of an organic base (triethyl amine) at ambient temperature (15-30° C.), the methods had the following disadvantages, which are undesirable for any commercial process. These are, i) the reaction required a period of more than 20-24 hours to proceed to completion, ii) the conversion to ceftiofur as indicated by monitoring of the reaction by HPLC was only about 88-90%, iii) about 9-10% of impurities were formed in the reaction, iv) the product i.e. ceftiofur was isolated as a gummy material, and v) the isolated product i.e. ceftiofur had a purity of only about 88% containing about 10-12% of impurites. Purification of the material thus obtained resulted in considerable loss thus giving ceftiofur (I) in low yield.

An improved method for synthesis of ceftriaxone comprising reaction of [2-(2-aminothiazol-4-yl)]-2-syn-methoxyimino acetic acid-2-benzothiazolyl thioester of formula (III) with a unprotected 7-amino-3-substituted cephalosporanic acid derivative i.e. 7-amino-3-(2,5-dihydro-6-hydroxy-2-methyl-5-oxo-1,2,4-triazin-3-yl)thiomethyl-3-cephem-4-carboxylic acid has been disclosed in U.S. Pat. No. 5,026,843 (Riccardo et. al.). The improvement comprises carrying out the said amidification reaction in a monophasic system comprising a mixture of a water-miscible organic solvent and water and in the presence of an organic base. The ceftriaxone thus obtained without isolation is converted into its sodium salt, which is isolated from the reaction mixture. The chemistry is summarized hereinbelow:

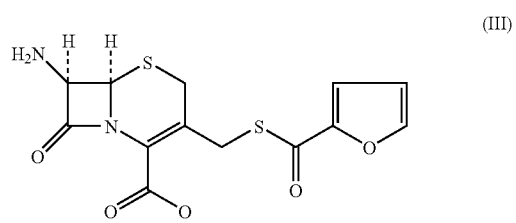

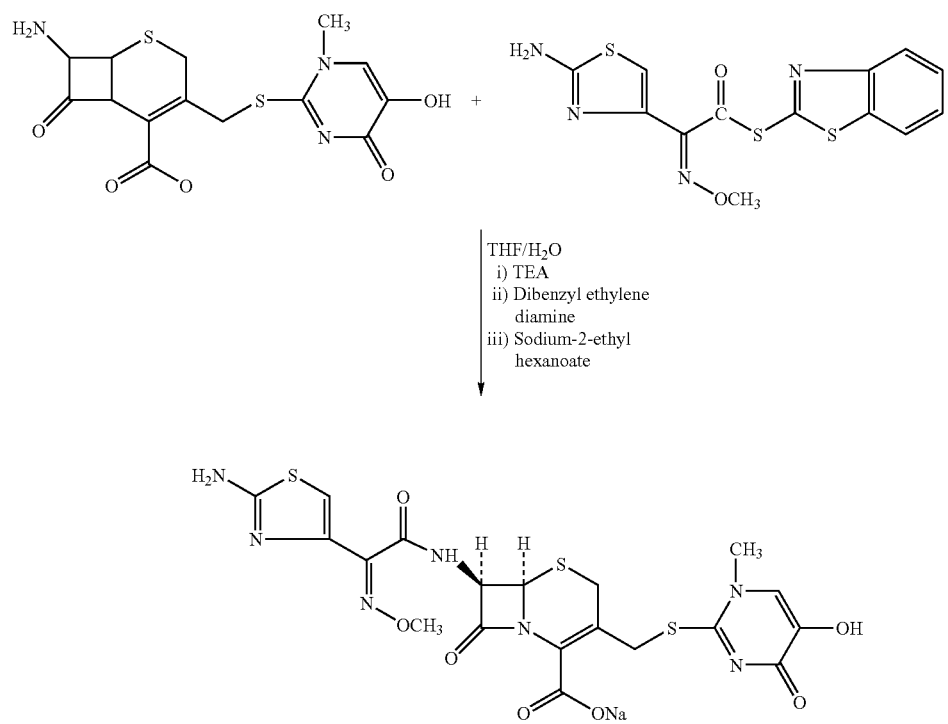

The water-miscible organic solvents listed in the U.S. Pat. No. 5,026,843 as useful for carrying out the abovementioned synthesis include tetrahydrofuran, dimethyl acetamide, dimethyl formamide, dioxane, dimethoxyethane. When these solvents are mixed with water, a homogeneous single phase would result. This helps in keeping the ceftiaxone thus produced in solution throughout the reaction and thereby, enabling a one-pot reaction for preparation of ceftriaxone sodium.

An attempt by the present inventors to extend the method described in U.S. Pat. No. 5,026,843 for synthesis of ceftiofur or ceftiofur sodium comprising reaction of [2-(2-aminothiazol-4-yl)]-2-methoxyimino acetic acid-2-benzothiazolyl thioester (MAEM) of formula (II) with 7-amino-3-thiofuroylmethyl-3-cephalosporanic acid of formula (III), -continued

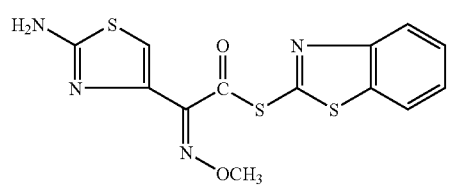

in a medium consisting of water and a water-miscible organic solvent disclosed in the said patent like tetrahydrofuran and N,N-dimethylacetamide, was however, not satisfactory and was found to give the product i.e. ceftiofur (I) associated with impurities in the level of 5-10% depending on the water-miscible organic solvent used. The product obtained was a sticky solid adhering to the sides of the reaction vessel, rendering its isolation as a solid very difficult.

In addition, replication of the methods exactly as described in U.S. Pat. Nos. 4,464,367 and 6,458,949 B1, referred herein earlier were also found to be associated with formation of higher level of impurities, which are to the tune of about 25-28% and 5-10% respectively.

The level of impurites formed in the-synthesis of ceftiofur by the four methods discussed herein before are summarized in Table-I.

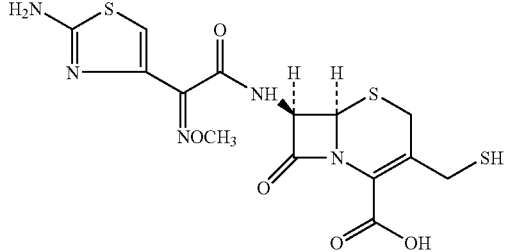

(V)

TABLE I

The level of impurities formed in the synthesis of ceftiofur (I) by various methods

| No. | Method | % Conversion | Total Impurities (%) | % Yield | Purity % |
|---|---|---|---|---|---|
| 1 | As per that described in U.S. Pat. No. 4,464,367 | 75 | 25-28 | Gummy material (not isolated) | — |
| 2 | As per that described in U.S. Pat. No. 6,458,949 B1 | 91.2 | 8.8 | 69.6 | 92.78 |
| 3 | Extrapolation of the method described in U.S. Pat. No. 4,767,852* | 89 | 11 | Sticky solid (not isolated) | — |
| 4 | Extrapolation of the method described in U.S. Pat. No. 5,026,843** | 93 | 5-10 | Sticky solid (not isolated) | — |

*reaction of (N,O)-bis silyl-7-amino-3-thiofuroylmethyl-3-cephalosporanic acid of formula (III$^1$) with [2-(2-aminothiazol-4-yl)]-2-methoxyimino acetic acid-2-benzothiazolyl thioester of formula (II) in dichloromethane at ambient temperature
**reaction of 7-amino-3-thiofuroylmethyl-3-cephalosporanic acid of formula (II) with [2-(2-aminothiazol-4-yl)]-2-methoxyimino acetic acid-2-benzothiazolyl thioester of formula (III) in a medium containing water and a water-miscible organic solvent in presence of a base It might be mentioned herein that the 3-thiofuroylmethyl substituent in ceftiofur, by virtue of it containing a carbonyl group interposed between a sulfur atom and a furan ring system is very labile in nature and is highly susceptible to fission of the sulfur-carbonyl bond as well as highly prone to undergo dimerisation, leading to formation of a dimeric compound in solution. This sets apart ceftiofur (I) from other 3-heterocyclic thiomethyl cephalosporin derivatives as described in U.S. Pat. No. 4,767,852 wherein the abovementioned lability is less pronounced or negligent and thereby ensuring their synthesis through any known methods.

The structure of the impurities arising out of fission of the sulfur-carbonyl bond and dimerization are given herein below as compounds (IV) and (V) respectively.

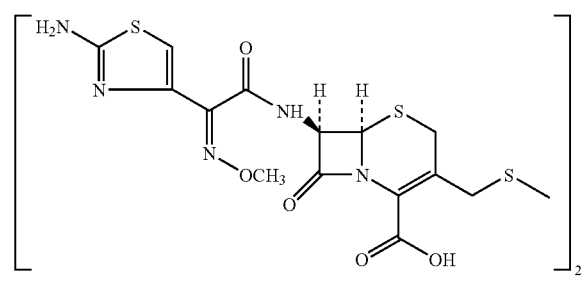

(IV)

Thus, to summarize, i) Synthesis of ceftiofur (I) had been achieved in prior art either through amidification at the 7-amino position of (a suitably protected) 7-amino-3-thiofuroylmethyl-3-cephalosporanic acid with [2-(2-aminothiazol-4-yl)]-2-methoxyimino acetic acid activated through formation of a mixed anhydride or through formation of an activated ester with 1-hydroxybenzotriazole, or 2-mercapto-5-phenyl-1, 3,4-oxadiazole and described respectively in U.S. Pat. Nos. 4,464,367 and 6,388,070 B1, summarized in Scheme-I and Scheme-III, or through amidification at the 7-amino position of (a suitably protected) 4-halo-2-methoxyimino-3-oxo butyric acid activated as the acid halide, followed by cyclization of the intermediate compound thus formed with thiourea, as described in U.S. Pat. No. 6,458,949 B1 and summarized in Scheme-II;

ii) Functionalization at 3-position of cefotaxime by reaction with thiofuroic acid, as summarized in Scheme-I, for the conversion of which, however, there is no enabling disclosure whatsoever in U.S. Pat. No. 4,464,367;

iii) Replication of both the abovementioned methods was found to give ceftiofur associated with impurities in the range of 5-28%;

iv) Extension of the methods described in U.S. Pat. Nos. 4,767,852 and 5,026,843 for synthesis of ceftiofur (I) was not only lengthy requiring about 18-24 hours but also lead to higher levels of impurity, resulting in a gummy material.

v) The abovementioned methods involve protection and deprotection of reactive functional groups, increasing the cost and time of manufacture;

vi) The product i.e. ceftiofur obtained by the abovementioned methods, because of the higher level of impurities is therefore not suitable for formulation into a suitable dosage form; and
vii) Removal of the impurities by purification leads to considerable loss of the product, increasing the cost of manufacture and rendering such methods commercially not attractive.

Further, since regulatory authorities all over the world are highly concerned about the level of impurities in a drug substance/drug product and are becoming increasingly stringent in approving products containing levels of impurities above the prescribed limits for human or animal consumption, it is imperative that any method of manufacture of a drug substance/drug product, apart from being commercially viable should provide the product conforming to pharmacopoeial specifications, containing amount of impurities within the prescribed limits or subatantially free of such impurities.

In view of the foregoing reasons, there exists a need for a vastly improved method for manufacture of ceftiofur (I), which not only satisfies the techno-commercial aspects i.e. cost-effectiveness, ease of operations, etc, but also provides a product of high purity, free of impurities and possess properties, which are amenable for formulation into a suitable dosage form.

The present inventors have found to their surprise that the existing need for an improved method for manufacture of ceftiofur in high yield and high purity could be achieved through:
i) carrying out amidifaction at 7-amino position of 7-amino-3-thiofuroylmethyl-3-cephalosporanic acid of formula (III) with [2-(2-aminothiazol-4-yl)]-2-methoxyimino acetic acid activated as its -2-benzothiazolyl ester of formula (II), obviating the need for protection and deprotection of reactive functional groups,
ii) the said amidification reaction is carried out in a system comprising mixture of a water-immiscible inert organic solvent and water i.e. a biphasic system and in the presence of a base, in a remarkably shorter time (1.5 to 3.0 hours) resulting in a product with substantially lower level of impurities,
iii) removal of most of the impurities formed during the above reaction in (ii) above, through a selective extraction method to provide ceftiofur (I) of high purity and substantially free of impurities by extraction of the aqueous mixture of the alkyl ammonium salt of ceftiofur (I) with a inert organic solvent.
iv) further removal of impurities formed during acidification of the alkyl ammonium salt of ceftiofur (I) with a mineral acid, in the presence of a mixture of water-miscible and water-immiscible solvent and in the presence of a saturated aqueous solution of an alkali or alkaline earth containing salt, by selectively partitioning ceftiofur (I) in the organic phase substantially free from impurities with the associated impurities getting extracted in the aqueous phase.

OBJECTS OF THE INVENTION

An object of the invention is to provide a method for manufacture of ceftiofur of formula (I) of high purity and substantially free of impurities.

Another object of the present invention is to provide a method for manufacture of ceftiofur of formula (I) comprising reaction of 7-amino-3-thiofuroylmethyl-3-cephalosporanic acid of formula (III) with [2-(2-aminothiazol-4-yl)]-2-methoxyimino acetic acid activated as its -2-benzothiazolyl ester of formula (II) in a biphasic system comprising mixture of a water-immiscible inert organic solvent and water and in the presence of base, wherein the formation of impurities is substantially minimized with concomitant higher conversion to the desired product.

Yet another object of the present invention is to provide a selective method for isolation of ceftiofur of formula (I), providing the product in high yield and high purity and substantially free of impurities.

SUMMARY OF THE INVENTION

In one aspect, the present invention provides a simple, cost-effective method for manufacture of ceftiofur of formula (I),

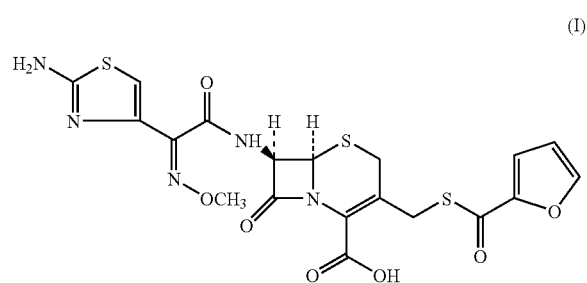

comprising reaction of [2-(2-aminothiazol-4-yl)]-2-methoxyimino acetic acid-2-benzothiazolyl ester of formula (II), and

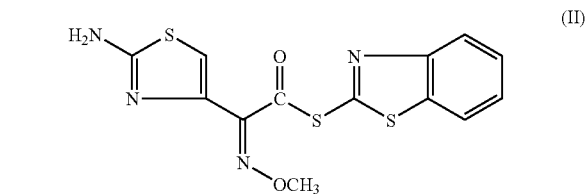

7-amino-3-thiofuroylmethyl-3-cephalosporanic acid of formula (III),

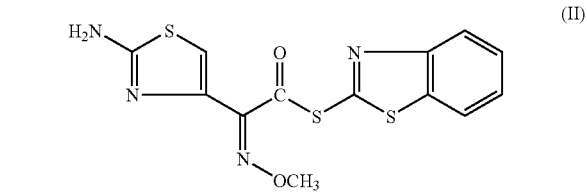

in the presence of a mixture comprising a water-immiscible inert organic solvent, and water and in the presence of a base and isolation to give ceftiofur of formula (I), in high purity and substantially free of impurities.

In another aspect, the present invention provides a method for isolation of ceftiofur of formula (I), in high purity and substantially free of impurities comprising,
i) addition of water to the reaction mixture and selective partitioning of the impurities in the organic phase and ceftiofur (I) in the form of a salt with the base in the aqueous phase, ii) acidification of the aqueous phase containing ceftiofur (I) in the form of a salt with the base in the presence of a mixture containing a water-miscible and a water-immiscible organic solvent and in the presence of a saturated aqueous solution of air alkali or alkaline earth containing salt, to partition ceftiofur (I) in the organic phase, and iii) isolation of ceftiofur (I) of high purity and substantially free of impurities by evaporation of the organic solvent or precipitation by addition of a co-solvent.

The method for preparation of ceftiofur (I) as per the present invention is summarized in Scheme-V for ready reference,

DETAILED DESCRIPTION OF THE INVENTION

The starting materials required are prepared by known methods. 7-Amino-3-thiomethyl furoyl-3-cephem-4-carboxylic acid of formula (III) can be prepared by the method disclosed in U.S. Pat. No. 4,937,330; comprising reaction of thiofuroic acid of formula (VI) with 7-amino cephalosporanic acid of formula (VII) at pH 6.4 and temperature of 65° C. in a mixture of water and an inert solvent such as ethyl acetate.

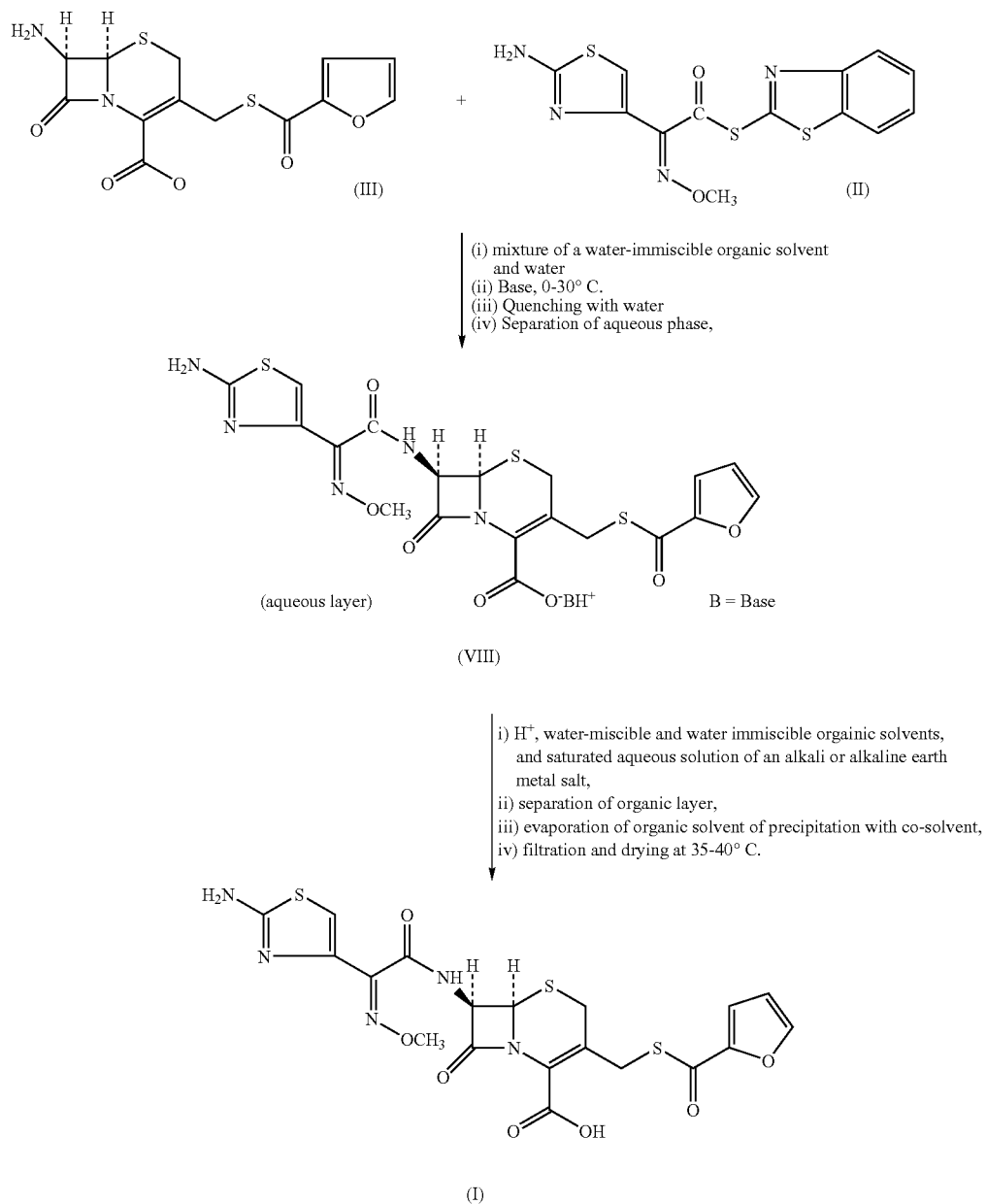

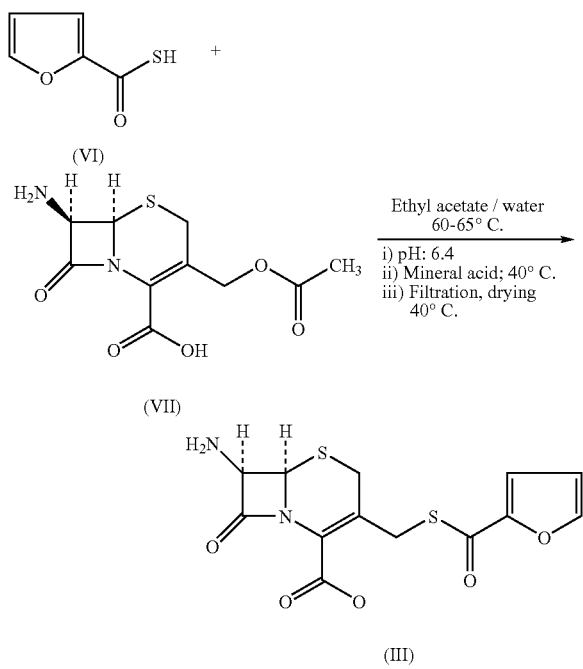

[2-(2-aminothiazol-4-yl)]-2-syn-methoxyimino acetic acid-2-benzothiazolyl thioester (MAEM) (II) can be prepared by the method described in EP Patent No. 0,037,380 comprising reaction of [2-(2-aminothiazol-4-yl)-2-syn-methoxyimino]acetic acid (IX) with bis[benzthiazolyl-(2)]disulphide (X) in the presence of triphenyl phosphine and dichloromethane as solvent at 0° C. The product (II) separating out is filtered, washed with dichloromethane followed by stirring with ethyl acetate at 0° C. and filtration to give [2-(2-aminothiazol-4-yl)]-2-syn-methoxyimino acetic acid-2-beizothiazolyl thioester of formula (II).

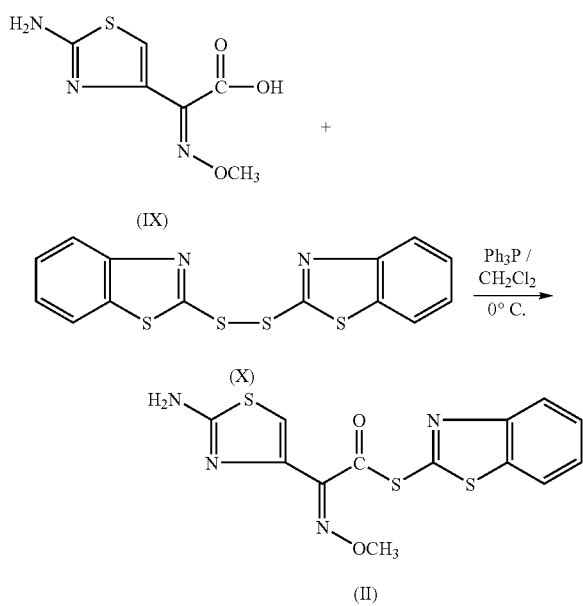

In a typical method for preparation of ceftiofur of formula (I), 7-amino-3-thiofuroylmethyl-3-cephalosporanic acid of formula (III) is added to a mixture of the water-immiscible inert organic solvent and water, followed by addition of the base. To the mixture is added [2-(2-aminothiazol-4-yl)]-2-methoxyimino acetic acid-2-benzothiazolyl ester of formula (II) and the reaction mixture agitated till completion of reaction to give ceftiofur of formula (I).

By definition an inert water-immiscible organic solvent is one, which does not participate in the reaction but helps facilitate smooth conversion of the reactants into the end product i.e. ceftiofur.

Typical of such water-immiscible inert organic solvents that can be employed are selected from chlorinated hydrocarbons such as dichloromethane, dichloroethane, chloroform etc While, any polar solvent, say a $C_{1-4}$ alkanol can be used instead of water for conducting the reaction in admixture with the water-immiscible inert organic solvent, resulting in a homogeneous phase, such polar solvents, however, do not contribute in reducing the formation of impurities. Water, on the other hand, when employed in admixture with a water-immiscible inert organic solvent ensures a heterogenous biphasic system, which substantially helps minimization of the impurities.

The addition of water helps in partial dissolution of the reactants as a result of which agitation of the reaction mass becomes easier. Asbence of water in the reaction medium makes agitation of the reaction mass very difficult.

The high selectivity of water over a $C_{1-4}$ alkanol in affecting the minimization of impurities can be understood form Table-II.

Table-II: The effect of water and a $C_{1-4}$ alkanol (methanol) in admixture with a water-immiscible inert organic solvent in the level of impurities formed in the method for preparation of ceftiofur (I) by reaction of 7-amino-3-thiofuroylmethyl-3-cephalosporanic acid of formula (III) with [2-(2-aminothiazol-4-yl)]-2-methoxyimino acetic acid-2-benzothiazolyl ester of formula (II)

| | | Impurities (%) | |
|---|---|---|---|
| No. | Reaction Medium | Formed in the reaction | Present in the isolated product |
| 1 | Water + Dichloromethane | 4.00 | 1.30 |
| 2 | Methanol + Dichloromethane | 11.00 | 4.00 |

While the ratio of the water-immiscible inert organic solvent to water can vary from 90:10 of the former to the latter to 98:2.0 of the same, the best results are obtained when the ratio is between 95:5.0 to 97.5:2.5 of the water-immiscible inert organic solvent to water.

For instance, the best results are obtained when the ratio of water-immiscible inert organic solvent to water is 97.5:2.5.

The dramatic effect brought about by the addition of water can be rationalised as follows:

7-amino-3-thiofuroylmethyl-3-cephalosporanic acid of formula (III) on addition of an organic base is converted to its alkyl ammonium salt (III$^2$), which is soluble in the aqueous phase. The alkyl ammonium salt (III$^2$) reacts with the compound of formula (II), which is soluble in the inert water immiscible solvent, apparently at the interface between the aqueous and organic phase thereby minimizing/eliminating side reactions by a mechanism which has not been clearly understood and facilitating higher conversion with lower impurity formation.

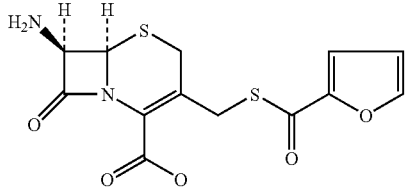

Interestingly enough, synthesis of ceftiofur of formula (I) has not been achieved earlier utilising a heterogenous biphasic system.

The reaction can be carried out a temperature ranging between low to ambient i.e. from 0° C. to 30° C., but preferably at a temperature ranging between 0° C. to 15° C.

Although any base can be used, organic bases are preferred. Typical of such bases that can be employed include triethylamine, tri-n-butylamine, tert-butylamine, dicyclohexylamine, N-methyl morpholine, 2,3-dimethylaminopyridine, N-methyl pyrrolidinone etc.

Among all the bases, tertiary amines are preferred which are selected from triethyl amine, tri-n-propyl amine, tri-n-butyl amine. Triethyl amine is preferred among the tertiary amines as impurity formation is minimized.

The rise in impurity formation by using organic bases having higher number of carbon atoms may be presumably due to the increase in the hydrophobicity of the trialkyl ammonium salt ($III^2$) with the increase in the number of carbon atoms in the trialkyl amine. This increase in hydrophobicity leads to increase in the solubility of the trialkyl ammonium salt ($III^2$) in the hydrophobic solvent due to which the acylation takes place in the hydrophobic solvent and not at the interphase between the aqueous phase and the hydrophobic phase resulting in a rise in the level of impurities.

The base can be employed in molar proportions of 1.0 mole to 3.0 moles per mole of compound of formula (III). Preferably the base is employed in molar proportions of 1.0 moles to 2.0 moles per mole of the compound of formula (III).

[2-(2-aminothiazol-4-yl)]-2-syn-methoxyimino acetic acid-2-benzothiazolyl thioester of formula (II) is employed in molar proportions of 1.0 to 2.0 moles per mole of the compound of formula (III), but preferably in a molar proportion of 1.0-1.5 moles.

The progress of the reaction can be monitored by TLC or HPLC and typically depending upon the temperature employed the reaction is over in a period ranging from 1.0 to 3.0 hours, with the monitoring system indicating more than 95% conversion to ceftiofur (I).

At the end of the reaction water is added, the aqueous layer is separated and further washed with a water-immiscible organic solvent selected from a chlorinated solvent such as dichloromethane, dichloroethane, chloroform or $C_{1-6}$ alkyl acetate like ethyl acetate, propyl acetate, n-butyl acetate at least once.

To the aqueous layer is added a mixture of a water-miscible solvent and a water-immiscible solvent, after separation of the organic layer.

The water-miscible organic solvent is selected from nitrites such as acetonitrile, propionitrile, butyronitrile or ketones such as acetone, methyl ethyl ketone or polar aprotic solvents like dimethyl sulphoxide, sulpholane. The preferred water-miscible solvent is a nitrile, preferably acetonitrile.

The water-immiscible solvent is selected from chlorinated solvents like dichloromethane, dichloroethane, chloroform or $C_{1-6}$ alkyl acetates like ethyl acetate, n-butyl acetate, isopropyl acetate but preferably ethyl acetate.

A mixture of alkyl acetate preferably ethyl acetate and nitrile preferably acetonitrile is added to the aqueous layer containing the alkyl ammonium salt of ceftiofur (I).

The ratio of the mixture of water-miscible solvent and water-immiscible solvent is between (1:1) and (5:1) but preferably the ratio of alkyl acetate and the polar aprotic solvent is (2:1 or 3:1).

The pH of the mixture is adjusted to 3.0±0.1 by addition of orthophosphoric acid and the mixture agitated further for complete liberating the ceftiofur (I) free acid from its corresponding salt with a organic base and taking it to the organic phase.

A mineral acid selected from hydrochloric acid, sulphuric acid, orthophosphoric acid but preferably orthophosphoric acid is added to the biphasic mixture.

A saturated solution of an alkali or an alkaline earth metal containing salt (15-30%) is added to the biphasic system and agitated at ambient temperature. The organic layer is separated and the aqueous layer is optionally again extracted with a mixture of water-miscible solvent and a water-immiscible solvent.

The alkali or an alkaline earth metal containing salt is selected from sodium chloride, sodium sulphate, potassium chloride, potassium sulphate, calcium chloride, but preferably sodium chloride.

Ceftiofur of formula (I) is isolated from the organic layer by evaporation of the organic solvent or by addition of a co-solvent.

The co-solvent added for precipitating out centiofur (I) at ambient temperature from the organic layer can be a non-polar aromatic solvent like toluene, xylene or aliphatic solvent like cyclohexane, n-hexane, heptane.

The mixture is agitated between 45-90 minutes but preferably 60 minutes for complete crystallization of pure ceftiofur (I). The pure compound (I) is filtered, washed with cyclohexane and dried at 35-40° C. The purity of ceftiofur (I) thus obtained has purity above 97% and substantially free from impurities such as the dimer compound (IV) and thiol compound (V).

Ceftiofur acid of formula (I) thus prepared, exhibits remarkable stability under stringent temperature and humidity conditions of 40±2° C. and relative humidity of 75%±5° C. even after 3 months of storage.

In a specific embodiment, 7-Amino-3-thiomethyl furoyl-3-cephem-4-carboxylic acid (1.0 mole) of formula (III) is added to dichloromethane and the mixture cooled between 0 and 5° C. Triethyl amine (1.8 moles) is added to the mixture followed by [2-(2-aminothiazol-4-yl)]-2-syn-methoxyimino acetic acid-2-benzothiazolyl thioester (1.2 moles) of formula (II) is added to the mixture with agitation. Water [0.4 times volume per gram of the compound of formula (III)] is added to the reaction mixture and agitated between 1.5 to 3.0 hours for the reaction to go to completion. The reaction mixture is quenched with water and the organic layer separated. The aqueous layer containing the salt of ceftiofur (I) is extracted with dichloromethane at least twice followed by extraction with ethyl acetate at least once.

A (2:1) mixture of ethyl acetate and acetonitrile is added to the aqueous layer and agitated at ambient temperature. The pH of the mixture is adjusted to 3.0±0.1 with orthophosphoric acid (30%) at ambient temperature. A 20% aqueous solution of sodium chloride is added to the biphasic mixture and agitated. The organic layer is separated and after optional treatment with activated carbon followed by filtration through celite bed is concentrated to isolate ceftiofur of formula (I). Alternately, cyclohexane is added to the organic layer and ceftiofur of formula (I) is allowed to precipitate completely at ambient temperature. The mixture is filtered and the wet cake washed with cyclohexane followed by drying at 35-40° C. to give ceftiofur (I) substantially free from impurities and with purity greater than 97%.

A comparison of the present method with that of prior art methods for preparation of ceftiofur (I) is given in Table-III.

Ceftiofur sodium can be prepared from ceftiofur acid (I) by methods disclosed in the prior art. Ceftiofur acid (I) prepared by the present method has been converted to its sodium salt by a method disclosed in a co-pending application No. 938/MUM/2002 dated Oct. 29, 2002.

Ceftiofur sodium prepared from ceftiofur acid (I) made by the present method has higher stability due to the lower level of impurities generated during the preparation of ceftiofur acid (I) and is also amenable to formulation as a dosage form.

The invention can be further illustrated by the following examples, which however should not be construed to be limiting the scope of the invention.

EXAMPLE 1

Preparation of (6R, 7R)-7-[[(2Z)-(2-amino-4-thiazolyl)(methoxyimino)acetyl]amino]-3-[[(2-furanylcarbonyl)thio]methyl]-8-oxo-5-thia-1-azabicyclo[4.2.0]oct-2-ene-2-carboxylic acid (I). (Mixture of Water Immiscible Solvent and Water in the Presence of Triethyl Amine as Base)

7-amino-3-(2-furanylcarbonylthiomethyl)-3-cephem-4-carboxylic acid(III) (100 gms; 0.294 moles) was added to

TABLE III

Synthesis of Ceftiofur (I) by the method of the present invention vis-à-vis the methods reported in prior art.

| No. | | Method of Present Invention | Method as described in U.S. Pat. No. 4,464,367 | Method as described in U.S. Pat. No. 6,458,949 | Method of U.S. Pat. No. 4,767,852, extrapolated for synthesis of ceftiofur (I). | Method of U.S. Pat. No. 5,026,843, extrapolated for synthesis of ceftiofur (I) |
|---|---|---|---|---|---|---|
| 1. | Steps required for making ceftiofur (I) | One step. Requiring no protection of the 2-amino group of [2-(2-aminothiazol-4-yl)]-2-synmethoxyimino acetic acid derivative. | Two steps. Requiring protection and deprotection of the 2-amino group of [2-(2-aminothiazol-4-yl)]-2-synmethoxyimino acetic acid derivative. | Seven steps starting from preparation of 4-halo-3-oxo-2-methoxyimino butyric acid. | One step starting from 7-amino-3-substituted-3-cephem carboxylic acid. | One step starting from 7-amino-3-substituted-3-cephem carboxylic acid. |
| 2. | Method for acylation of the 7-amino group | With [2-(2-aminothiazol-4-yl)-2-syn-methoxyimino] acetic acid (IX) as its 2-mercaptobenzothiazole ester. | With [2-(2-aminothiazol-4-yl)-2-syn-methoxyimino] acetic acid (IX) activated as 1-Hydroxy benzotriazole derivative in presence of dicyclohexyl carbodiimide. | With 4-halo-3-oxo-2-methoxyimino butyric halide on silylated 7-amino-3-[2-furyl carbonylthiomethyl]-3-cephem-4-carboxylic acid | With [2-(2-aminothiazol-4-yl)-2-syn-methoxyimino] acetic acid (IX) as its 2-mercaptobenzothiazole ester | With [2-(2-aminothiazol-4-yl)-2-syn-methoxyimino] acetic acid (IX) as its 2-mercaptobenzothiazole ester |
| 3. | Reaction time | Between 1.5 to 3.0 hours | Between 2.0 to 4.0 hours | Between 2.0 to 4.0 hours. | Between 18 to 24 hours | Between 2.0 to 4.0 hours |
| 4. | Level of impurities | 4.0 to 5.0% | 26.0 to 29.0% | 7.0 to 8.0% | 8.0 to 10.0% | 8.0 to 10.0% |
| 4. | Level of impurities formed during the reaction | 4.0 to 5.0% | 26.0 to 29.0% | 7.0 to 8.0% | 8.0 to 10.0% | 8.0 to 10.0% |
| 5. | Level of impurities in isolated ceftiofur (I) | 1.5 to 3.0% | ≈28.0% | 7.0% | — gummy solid (not isolated) | — gummy solid (not isolated) |
| 6. | Purity of ceftiofur (I) | greater than 97%. | — | between 90-95% | — | — |
| 7. | Stability of ceftiofur sodium prepared from the acid (I) | Stable for 3 months at 40 ± 2° C. and relative humidity 75% ± 5 | Impurity level is quite high, therefore, stability is low. | Starts degrading in the first month at 40 ± 2° C. and relative humidity 75% ± 5; purity falls below specified limits in the first month itself. | — | — | dichloromethane (1000 ml). The reaction mixture was cooled to 0° C. and triethyl amine (53.57 gms; 0.529 moles) was added at 0-5° C. in 60 minutes. [2-(2-aminothiazol-4-yl)]-2-syn-methoxyimino acetic acid-2-benzothiazolyl thioester (II) (123.5 gms; 0.353 moles) was added and agitated for 15 minutes. Water (25.0 ml) was added to the mixture and agitated at 5-7° C. The reaction was monitored by HPLC and the mixture stirred till compound (III) was less than 1.0% on HPLC. The reaction mixture was worked up by adding water (700 ml) and stirred for 15 minutes at 10-15° C. The aqueous layer was separated and washed thrice with dichloromethane (300 ml). The aqueous layer was then again washed with ethyl acetate (300 ml). The aqueous layer was separated and a mixture of ethyl acetate (2000 ml) and acetonitrile (1000 ml) were added to the aqueous layer. The pH was adjusted to 3.0 by adding 25% orthophosphoric acid in 30 minutes at 15-20° C. A concentrated solution of sodium chloride (25%) was added to the biphasic mixture and the resulting biphasic mixture was agitated for 30 minutes. The organic layer was separated and the aqueous layer re-extracted with a (2:1) mixture of ethyl acetate and acetonitrile (750 ml). The organic layers were combined and washed with 5% brine solution. The organic layer was separated and after optional carbon treatment followed by filtration was dried on sodium sulphate. The organic layer was evaporated and a mixture of ethyl acetate (300 ml) and cyclohexane (1500 ml) was added to the residue and agitated at 20-25° C. for 60 minutes. The product (I) was filtered and washed twice with cyclohexane (200 ml). The product was dried at 35-40° C. under reduced pressure to give 100.3 gms of ceftiofur (I). % yield: 66.95; Purity: 98.5%. Total impurity: 1.50%

EXAMPLE 2

Preparation of (6R, 7R)-7-[[(2Z)-(2-amino-4-thiazolyl)(methoxyimino)acetyl]amino]-3-[[(2-furanylcarbonyl)thio]methyl]-8-oxo-5-thia-1-azabicyclo[4.2.0]oct-2-ene-2-carboxylic acid (I) (Water Immiscible Solvent and Water Miscible Solvent Without Water)

7-amino-3-(2-furanylcarbonylthiomethyl)-3-cephem-4-carboxylic acid (III) (5.0 gms; 0.0147 moles) was added to dichloromethane (50 ml). The reaction mixture was cooled to 0° C. and [2-(2-aminothiazol-4-yl)]-2-syn-methoxyimino acetic acid-2-benzothiazolyl thioester (II) (5.4 gms; 0.0154 moles) was added to the mixture with agitation. Triethyl amine (2.67 gms; 0.0264 moles) was added to the mixture followed by methanol (2.5 ml). The reaction mixture was monitored by HPLC and stirred for 3.0 hours at 5±2° C.; the reaction was not going to completion as 2.5% was remaining unreacted even after stirring further for 2.0 hours. The reaction mixture was quenched with water. The aqueous layer was washed with dichloromethane (45 ml) at least once followed by washing with ethyl acetate (45 ml). Ethyl acetate (15 ml) was added to the aqueous layer and the pH was adjusted to pH 3 with 30% orthophospl-ioric acid. The organic layer was separated dried on sodium sulphate and evaporated between 25-30° C. under reduced pressure. A mixture of ethyl acetate (300 ml) and cyclohexane (1500 ml) was added to the residue and agitated at 20-25° C. for 60 minutes. The product (I) was filtered and washed twice with cyclohexane (200 ml). The product was dried at 35-40° C. under reduced pressure to give 4.66 gms. % yield: 64.5%; Purity: 96.1%. Total impurity: 3.9%.

We claim:

1. A process for preparation of ceftiofur of formula (I) of a purity greater than 97%

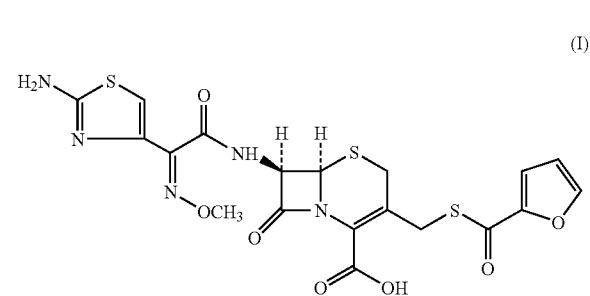

comprising the steps of: reacting [2-(2-aminothiazol-4-yl)]-2-syn-methoxyimino acetic acid-2-benzothiazolyl thioester of formula (II),

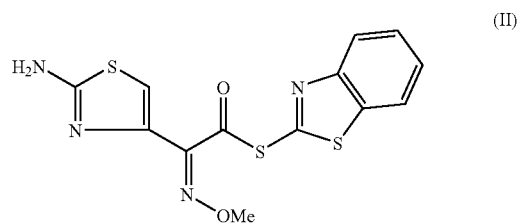

with 7-amino-3-(2-furanylcarbonylthiomethyl)-3-cephem-4-carboxylic acid of formula (III)

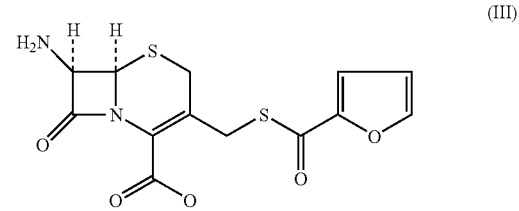

in the presence of a mixture of an water-immiscible inert organic solvent and water and in the presence of a organic base and isolating ceftiofur of formula (I) of a purity greater than 97% by,
   a) adding water to the reaction mixture and selectively partitioning the impurities in the organic phase and ceftiofur (I) in the form of a salt with the base in the aqueous phase,
   b) acidifying the aqueous phase containing ceftiofur (I) in the form of a salt with the base in the presence of a mixture containing a water-miscible and a water-immiscible organic solvent and in the presence of a saturated aqueous solution of an alkali or alkaline earth containing salt, to partition ceftiofur (I) in the organic phase, and
   c) isolating ceftiofur (I) of a purity greater than 97% by evaporation of the organic solvent or precipitation by addition of an anti-solvent.

2. The process according to claim 1, wherein the water-immiscible inert organic solvent comprises a chlorinated solvent.

3. The process according to claim 2, wherein said chlorinated solvent is selected from dichloromethane, 1,2-dichloroethane, and chloroform.

4. The process according to claim 1, wherein the organic base is selected from triethyl amine, N-methyl morpholine, tert-butyl amine, dicyclohexyl amine, tri-n-butylamine, N-methyl pyrrolidinone and 2,3-dimethylamino pyridine.

5. The process according to claim 4, wherein the base is employed in molar proportion of 1.0 to 3.0 moles per mole of the compound of formula (III).

6. The process according to claim 1, wherein the compound of formula (II) is employed in molar proportion of 1.0 to 2.0 moles per mole of the compound of formula (III).

7. The process according to claim 1, wherein the ratio of the water-immiscible inert organic solvent to water is between 90:10 and 98:2.0.

8. The process according to claim 7, wherein the ratio of the water-immiscible inert organic solvent and to water is between 95:5.0 and 97.5:2.5.

9. The process according to claim 1, wherein the temperature at which the reaction is carried out is between 0 and 30° C.

10. The process according to claim 1, wherein the water-immiscible solvent is a chlorinated solvent or $C_{1-6}$ alkyl acetate.

11. The process according to claim 10, wherein the chlorinated inert organic solvent is selected from dichloromethane, dichloroethane and chloroform and the $C_{1-6}$ alkyl acetate is selected from ethyl acetate, butyl acetate, n-propyl acetate, isopropyl acetate and tert-butyl acetate.

12. The process according to claim 1, wherein the acid employed is a mineral acid selected from orthophosphoric acid, hydrochloric acid and sulphuric acid.

13. The process according to claim 1, wherein the pH of the reaction in step (b) is 3.0±0.1.

14. The process according to claim 1, wherein the water-miscible organic solvent is selected from a ketonic solvent and a nitrile.

15. The process according to claim 1, wherein the water-miscible organic solvent is a nitrile selected from acetonitrile, propionitrile and butyronitrile.

16. The process according to claim 1, wherein the water immiscible solvent is selected from dichloromethane, dichloroethane, chloroform, ethyl acetate, n-butyl acetate and isopropyl acetate.

17. The process according to claim 1, wherein the alkali or an alkaline earth metal containing salt is selected from sodium chloride, potassium chloride, sodium sulphate, potassium sulphate and calcium chloride.

18. The process according to claim 1, wherein the antisolvent is selected from an aromatic hydrocarbon and an aliphatic hydrocarbon.

19. The process according to claim 18, wherein the aromatic hydrocarbon is selected from toluene and xylene, and the aliphatic hydrocarbon is selected from cyclohexane, n-hexane and heptane.

* * * * *